(12) United States Patent
Kaplan et al.

(10) Patent No.: US 6,566,469 B1
(45) Date of Patent: May 20, 2003

(54) ENZYME-MEDIATED POLYMERIZATION METHODS AND PRODUCTS

(75) Inventors: David Kaplan, Loveland, MA (US); Graham Swift, Brooklyn, NY (US); Richard A. Gross, Brooklyn, NY (US); Bhanu Kalra, Blue Bell, PA (US)

(73) Assignees: Trustees of Tufts College, Medford, MA (US); Rohm & Haas Company, Philadelphia, PA (US); Polytechnic Institute of New York, Brooklyn, NY (US)

( * ) Notice: Subject to any disclaimer, the term of this patent is extended or adjusted under 35 U.S.C. 154(b) by 0 days.

(21) Appl. No.: 09/602,649

(22) Filed: Jun. 22, 2000

Related U.S. Application Data

(60) Provisional application No. 60/140,221, filed on Jun. 22, 1999, and provisional application No. 60/146,284, filed on Jul. 29, 1999.

(51) Int. Cl.$^7$ .................................................. C08F 4/30
(52) U.S. Cl. .................... 526/229; 526/89; 526/199; 526/208; 526/303.1; 526/310; 526/317.1; 526/318; 526/319; 526/329.2; 526/227
(58) Field of Search ................................ 526/199, 229, 526/303.1, 227, 310, 317.1, 318, 319, 329.2, 208, 89

(56) References Cited

U.S. PATENT DOCUMENTS 5,973,203 A * 10/1999 Ergaz et al. ................ 564/135
6,022,500 A * 2/2000 John et al. .................. 264/4.1
6,096,859 A * 8/2000 Akkara et al. .............. 528/501

FOREIGN PATENT DOCUMENTS

JP 08333420 12/1996

OTHER PUBLICATIONS

Derango et al.; " Enzyme–Mediated Polymerization of Acrylic Monomers", Biotechnology Techniques, 6(6): 523–526, (Nov./Dec. 1992).

Dordick S. Jonathan; "Enzyme–Derived Polymers: New Materials for the 21$^{st}$ Century", Polymeric Materials Science and Engineering, 74: 1 (1996).

Emery et al.; " Free–Radical Polymerization of Acrylamide by Horseradish Peroxidase–Mediated Initiation", Journal of Polymer Science, Part A. Polymer Chemistry 35: 331–333, (1997).

Kalra and Gross; Enzymatic Synthesis of Predominantly Syndiotactic Poly(Methyl Methacrylate), Polymer Preprints, 41 (1): 213, (2000).

Kalra and Gross; Enzymatic Synthesis of Predominantly Syndiotactic Poly(Methyl Methacrylate), Book of Abstracts, 219$^{th}$ ACS National Meeting, San Francisco, CA , Mar. 26–30, 2000.

Kitayama et al.; "Highly Syndiotactic Poly(methyl methacrylate). With narrow molecular weight distribution formed by tert–butyllithium–trialkylaluminium in Toluene", Polymer Bulletin, 20 pp. 505–510 (1988).

Lalot et al.; " A Kinetic Approach to Acrylamide Radical Polymerization by Horse Radish Peroxidase–mediated Initiation ", Polymer Int. 48: 288–292 (1999).

Uyama et al.; " Chemoselective Polymerization of a Phenol Derivative Having a Methacryl Group by Peroxidase Catalyst", Macromolecules, 31 (2): 554–556 (1998).

Teixeira et al.; " β–Diketones as Key Compounds in Free–Radical Polymerization by Enzyme–Mediated Initiation".

* cited by examiner

*Primary Examiner*—Tatyana Zalukaeva
(74) *Attorney, Agent, or Firm*—Ropes & Gray

(57) ABSTRACT

A method for polymerization of substituted ethylene monomers in an enzyme-mediated process is disclosed. The reaction proceeds under mild conditions with a wide variety of monomers, and is capable of producing stereoregular polymers. In certain embodiments, no organic solvent is necessary.

22 Claims, 9 Drawing Sheets

US 6,566,469 B1

ENZYME-MEDIATED POLYMERIZATION METHODS AND PRODUCTS

This application is based on U.S. Provisional Applications No. 60/140,221, filed Jun. 22, 1999, and No. 60/146,284, filed Jul. 29, 1999, the specifications of which are hereby incorporated herein by reference.

FIELD OF THE INVENTION

The invention relates to enzyme-mediated polymerization methods and products, particularly regarding polymerization of substituted ethylene monomers, even more particularly in the presence of a peroxide source.

BACKGROUND OF THE INVENTION

Polymerization processes have made possible many advances in materials science, especially plastics, that have transformed the world in a matter of decades. Most polymerization processes can be categorized into four distinct groups, based on the mechanism of the polymerization reaction. One of the most widely utilized of these processes is free-radical polymerization, wherein, typically, an initiator, such as benzoyl peroxide, is thermally dissociated to provide a radical source that begins the polymerization process, wherein the reactive terminus of the growing polymer chain is characterized by having an unpaired electron. Anionic and cationic processes may be initiated by nucleophiles and Lewis acids, respectively, and the reactive terminus of the growing polymer chain is characterized by being nucleophilic in an anionic process, and by being electrophilic in a cationic process. The fourth category includes transition metal-mediated processes, such as Ziegler-Natta polymerizations, wherein the reactive terminus of the growing polymer chain is associated with a transition metal catalyst.

The monomer undergoing polymerization determines, in part, the mechanism of the polymerization. For example, polystyrene, commonly used for insulation, packing materials, and a variety of other applications, can be formed from styrene utilizing any of the above mechanisms. As of now, the free-radical process is most commonly used for large-scale industrial processes. Most of the processes except Zeigler-Natta polymerization produce atactic, amorphous polystyrene. Atactic describes a polymer comprising a series of stereogenic carbons wherein the stereochemistry of successive stereogenic carbons is irregular or random. Isotactic describes a polymer wherein successive stereogenic carbons tend to have the same stereochemical designation, e.g., RRRRR. Syndiotactic, on the other hand, describes a polymer wherein successive stereogenic carbons alternate in stereochemical designation, e.g., RSRSRSRS. Zeigler-Natta polymerizations can produce either isotactic or syndiotactic polystyrene, depending on the catalyst and reaction conditions.

Anionic polymerization of styrene, as described in U.S. Pat. No. 4,859,748 to Dow Chemical Company, may be initiated by n-butyllithium (NBL), and the molecular weight (MW) of the resulting polymer can be controlled by varying the ratio of monomer to initiator. Polymerization may be terminated by adding an electrophile, such as carbon dioxide, to react with the anionic terminus of the growing polymer chains. However, n-butyllithium is highly reactive and potentially dangerous, and requires the use of toxic organic solvents in the reaction medium.

The cationic polymerization of styrene has proved difficult because the fast termination rates make high molecular weight polymers difficult to obtain, as described in U.S. Pat. Nos. 4,087,599, 4,112,209, and 4,161,573 to Dow Chemical Company, and so this process has not been commonly employed in industry. A typical Lewis acid initiator is $BF_3$, using water as a cocatalyst. Again, this protocol prevents the use of water as a solvent, and relies instead on toxic organic solvents.

As stated above, isotactic and syntiotactic polystyrene are available through Zeigler-Natta polymerization of styrene. N. Ishihara et al., *Macromolecules*, 19, 2464, 1986, and U.S. Pat. Nos. 5,064,918, 5,045,517, and 5,196,490 to Dow Chemical Company. The isotactic form may be produced by using an aluminum-activated $TiCl_3$ catalyst, and syndiotactic form may be prepared using soluble titanium complexes, such as $(\eta^5—C_5H_5)TiCl_3$, in combination with a partially hydrolyzed alkylaluminum, such as methylalumoxane. The reaction may be performed in the absence of solvent, or in organic solvents such as benzene, toluene, pentane, hexane. The molecular weight of the resulting polymer may be varied by changing the catalyst, amount of catalyst, and amount of monomer charged. Because of the sensitivity of the catalyst systems, these procedures require that the starting materials be highly purified, and water may not be present in the reaction mixture. Also, the final product typically must be separated from the metal catalyst.

For example, free-radical polymerization of styrene, such as described in U.S. Pat. No. 5,145,924 to Dow Chemical Company, may be used to produce atactic, amorphous polystyrene in a wide range of molecular weights. Higher molecular weight polymers can conveniently prepared using anionic polymerization. However, due to the faster reaction rates and shorter reaction times required for an analogous free-radical process, polystyrene can be made more inexpensively using a free-radical process. The starting materials need not be purified and initiator residues need not be removed, adding to the convenience of free-radical techniques. The molecular weight of the product polymer may be controlled by using different initiators, changing the reaction temperature (generally 100–170° C.), or adding chain transfer agents, such as ethylbenzene. The high reaction temperatures involved generally preclude the use of aqueous solvent, and so such procedures often use toxic organic solvents.

Polyacrylamide, another commercially useful polymer (see, for example, U.S. Pat. Nos. 5,868,087, 5,863,650, and 5,873,991), is typically produced by a highly exothermic free-radical process in aqueous medium. The quantity of heat generated is normally handled in one of two ways: the reaction temperature is permitted to rise to around 90° C. in a standard cooled reaction vessel, or the reaction is conducted in thin films to provide a high surface area-to-volume ratio for heat dispersion, thereby limiting the temperature increase. Additional techniques for producing polyacrylamide are described in U.S. Pat. Nos. 4,138,839 and 4,132,844 to American Cyanamid Company. U.S. Pat. No. 4,439,332 to American Cyanamid further describes a technique for copolymerizing acrylamide with acrylic acid in an inverse emulsion process using sorbitan monooleate as a surfactant. This technique helps to avoid high solution viscosities.

Polymers of acrylate, methacrylate, and related esters, are typically manufactured using free-radical processes from the requisite monomers. Polymethylmethacrylate is also known as Lucite® and Plexiglas®. Copolymers are often produced for their superior properties. The resulting polymers are atactic. Methacrylic polymers are often prepared in the absence of solvent, the method of choice for production of sheets, rods, tubes, molding and extrusion compounds, as described in U.S. Pat. Nos. 3,113,114 to DuPont, 3,382,209 to American Cyanamid, and 3,376,371 to Swedlow Inc. Both acrylic and methacrylic polymers may be prepared using an organic solvent, such as benzene, toluene, isopropyl alcohol, isobutyl alcohol, chloroform, orcarbon tetrachloride. The molecular weight can be controlled by using a chain transfer agent, changing the radical initiator, concentrations of the monomers or initiator, the solvent, or the temperature. Typical reaction times are several hours (for methacrylates) to 24 hours (for acrylates). Reaction temperatures are higher for methacrylates (e.g., 140° C.) than for acrylate polymers (e.g., 80° C.). Emulsion polymerization is an even more common method for polymerization of these monomers, accounting for 70% of acrylate monomer consumption. No solvents are required and the reaction is much more rapid than the analogous solution-phase process, typically proceeding to completion in several hours. Reaction temperatures are generally 75–90° C. U.S. Pat. Nos. 3,458,466 to Dow Chemical Company and 3,344,100 to B.F. Goodrich.

Anionic polymerization is also possible for acrylate and methacrylate monomers, particularly for generating tactic methacrylic polymers of narrow PDI and controlled molecular architecture. Organometallic compounds such as n-butyllithium are used as initiators. Nonpolar solvents usually yield isotactic polymers while in polar solvents syndiotactic polymers usually result. The reaction conditions must be carefully controlled to obtain high degrees of stereoregularity. This method has not, however, found significant commercial utility, and again requires the use of toxic organic solvents.

A general method for producing polymers of substituted ethylenes such as styrene, acrylamide, and acrylate and methacrylate esters that does not require the use of high temperatures, toxic organic solvents, reactive reagents, or rigorous purification of starting materials or products would provide a convenient polymerization process. Such a process that generated stereoregular polymers would be a further advance.

SUMMARY OF THE INVENTION

The present invention pertains to the use of peroxidases such as horseradish peroxidase (HRP), soybean peroxidases, and a diversity of related enzymes in the catalysis of vinyl monomer polymerizations. The polymerizations may be performed at ambient temperature in the presence of low concentrations of hydrogen peroxide and a reducing substrate. Polymers formed by this method may have very high molecular weights. By this method, high molecular weight polymers can be formed rapidly and at room temperature. Furthermore, this procedure may be used to produce stereoregular polymers. The present method tolerates a range of reaction conditions, including emulsion and reverse emulsion conditions. Moreover, the present method may be applied to the preparation of a wide range of copolymers, such as MMA with acrylamide and MMA with sodium acrylate. In certain embodiments, the present method may be used to prepare cross-linked polymers.

Thus, in one embodiment, the invention provides a method for polymerizing substituted ethylene monomers by combining at least one substituted ethylene monomer, a peroxide source, an enzyme, a transfer agent, and an organic solvent. The peroxide source may be hydrogen peroxide. The enzyme may be horseradish peroxidase, soybean peroxidase, or lignin peroxidase. The substituted ethylene monomer may be a methacrylate ester, acrylate ester, acrylamide, styrene, acrylic acid, or a salt thereof. The organic solvent may be tetrahydrofuran (THF), dimethyl formamide (DMF), acetone, or dioxane. The method may be performed using an emulsion or an inverse emulsion. The transfer agent may comprise a β-dicarbonyl. The enzyme may be a recombinant enzyme, a thermophilic enzyme, a mesophilic enzyme, or an enzyme active below 0° C.

In another embodiment, the invention provides a method for polymerizing substituted ethylene monomers by combining at least one substituted ethylene monomer, a peroxide source, an enzyme such as soybean peroxidase, chloroperoxidase, xanthine oxidase, or alcohol oxidase, and a transfer agent. The various reagents, solvents, and conditions may be selected as outlined above.

In yet another embodiment, the invention provides a method for polymerizing substituted ethylene monomers by combining under an inert atmosphere at least one substituted ethylene monomer, a peroxide source, an enzyme, and a transfer agent. The various reagents, solvents, and conditions may be selected as outlined above.

In still another embodiment, the invention provides a method for copolymerizing substituted ethylene monomers by combining at least two substituted ethylene monomers, a peroxide source, an enzyme, and a transfer agent. The various reagents, solvents, and conditions may be selected as outlined above.

In a further embodiment, the invention provides a method for polymerizing substituted ethylene monomers, comprising combining at least one substituted ethylene monomer, a peroxide source, an enzyme, and a transfer agent to produce a polymer at least 85% isotactic or at least 85% syndiotactic. The various reagents, solvents, and conditions may be selected as outlined above.

In another embodiment, the invention also provides a method for polymerizing a compound of the general formula (I):

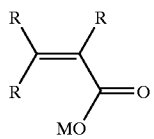

wherein
- M represents H, an alkali metal, an alkaline earth metal, or an ammonium counterion, and
- R represents, independently for each occurrence, H, a halogen, a ketone, an aldehyde, an ester, an amide, a carboxyl, a sulfonyl, a sulfoxide, an acylamino, a lower alkyl group, a lower alkenyl group, a lower alkynyl group, or an aryl group, comprising combining a compound of the general formula (I), a peroxide source, an enzyme capable of generating a radical in the presence of a peroxide, and a transfer agent.

The various reagents, solvents, and conditions may be selected as outlined above.

In another aspect, the invention provides a poly (methacrylate ester) which is at least 85% syndiotactic, such as a polymer produced by one of the methods outlined above.

DETAILED DESCRIPTION OF THE INVENTION

I. General

Figure 1:
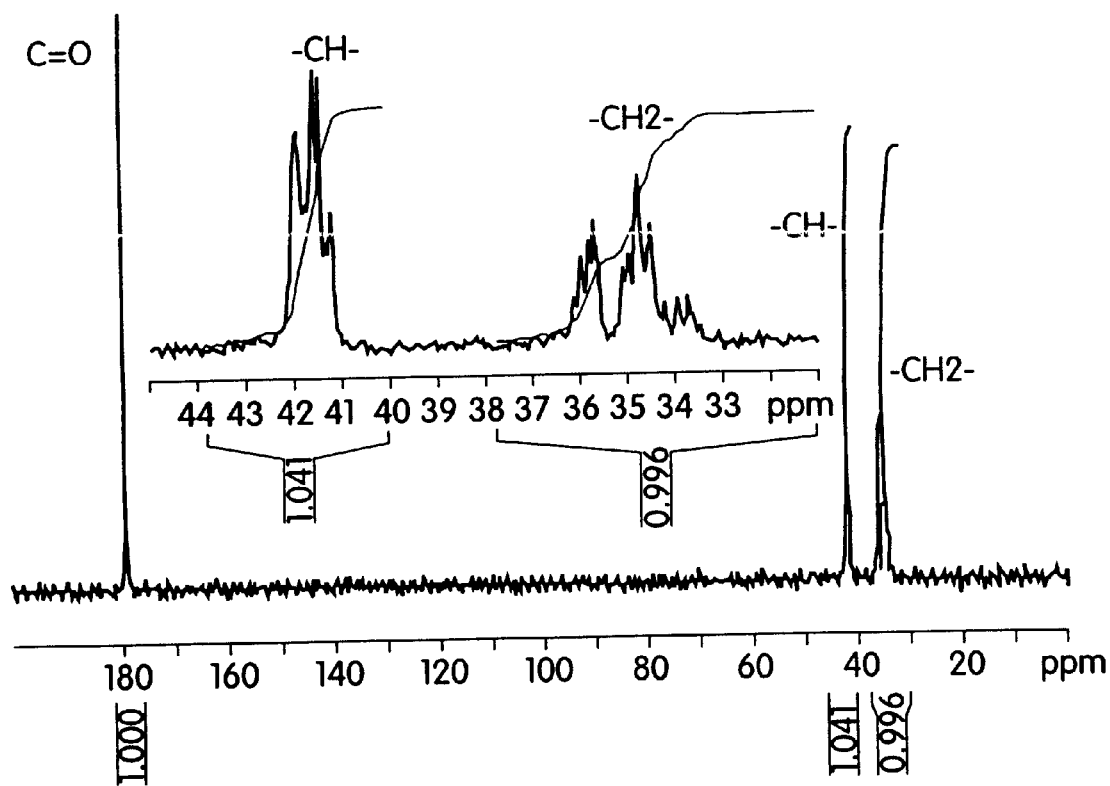
FIG. 1 is a $^{13}$C-NMR spectrum of atatic poly(acrylamide) in D$_2$O prepared by a method described herein.
Figure 2:
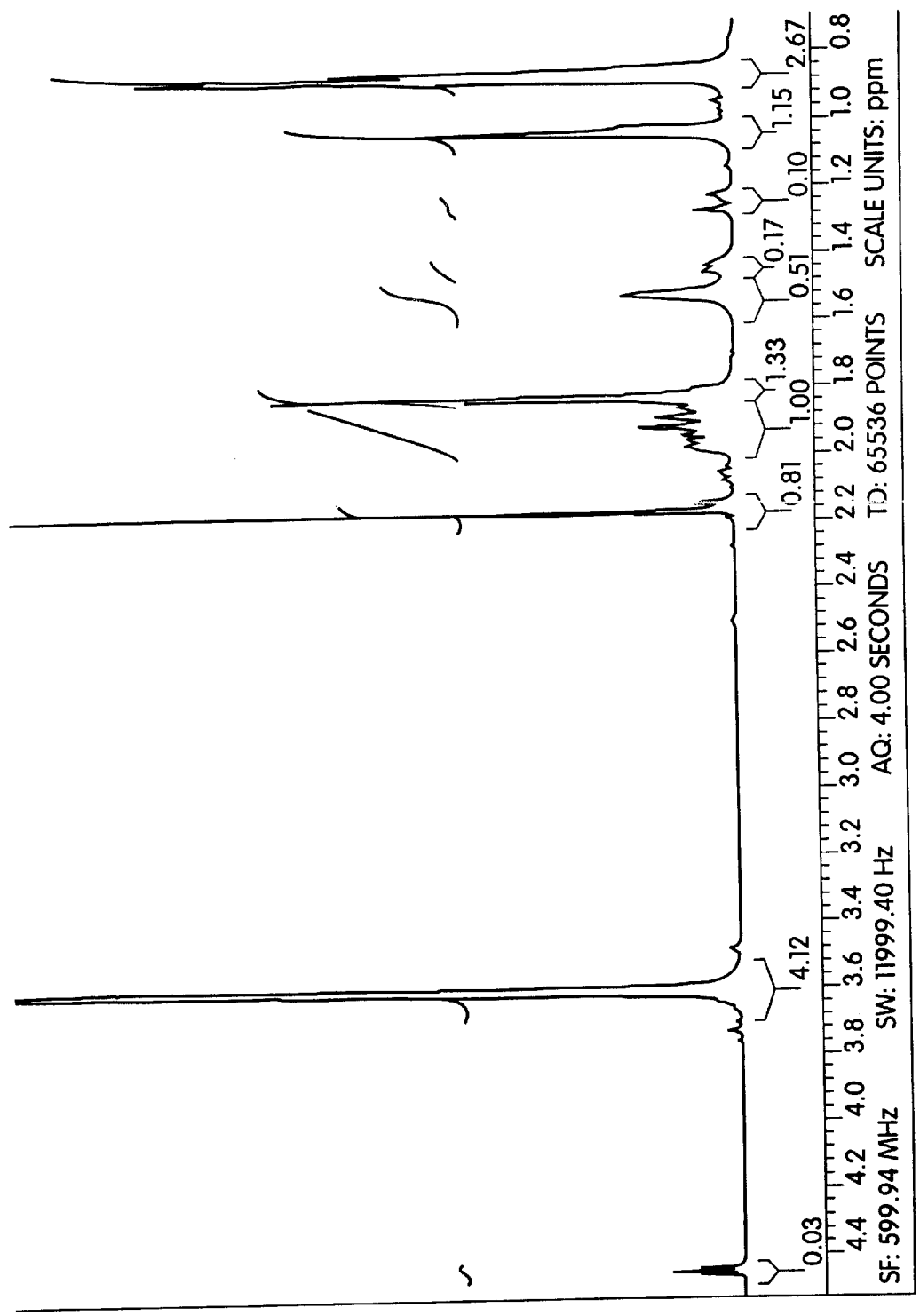
FIG. 2 is a $^1$H-NMR spectrum of poly(methyl methacrylate) (PMMA) in CDCl$_3$ prepared by a method described herein.

The features and other details of the invention, either as steps of the invention or as combinations of parts of the invention, will now be more particularly described and pointed out. It will be understood that the particular embodiments of the invention are shown by way of illustration and not as limitations of the invention. The principle features of this invention can be employed in various embodiments without departing from the scope of the invention.

The present invention relates to a method of forming polymers and copolymers of various vinyl monomers in an enzyme-mediated process. In certain embodiments, high molecular weight polymers are produced. A high molecular weight polymer, as defined herein, is a polymer having a number average molecular weight ($M_n$) of greater than or equal to about 5,000 grams/mole. The present invention also relates to a method for forming polymers and copolymers of various acrylates that have a predominantly stereoregular chain structure. Examples of stereoregular chains are those that have predominantly isotactic or syndiotactic repeat unit sequences.

II. Description of Selected Embodiments

Definitions:

The term "heteroatom" as used herein means an atom of any element other than carbon or hydrogen. Preferred heteroatoms are boron, nitrogen, oxygen, phosphorus, sulfur and selenium.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring 5 structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, alkylaminos, carbonyl-substituted alkyls, —CF$_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively. When not otherwise indicated, the terms alkenyl and alkynyl will preferably refer to lower alkenyl and lower alkynyl groups, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, isoxazole, triazole, pyrazole, pyridine, pyrazine, pyridazine and pyrimidine, and the like. Those aryl groups having heteroatoms in the ring structure may also be referred to as "aryl heterocycles", "heteroaryls", or "heteroaromatics". The term "aryl" refers to both substituted and unsubstituted aromatic rings. The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl, and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocycle" refer to 4- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, hydantoin, oxazoline, imidazolinetrione, triazolinone, quinoline, phthalazine, naphthyridine, quinoxaline, quinazoline, quinoline, pteridine, carbazole, carboline, phenanthridine, acridine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

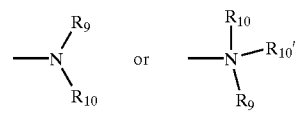

wherein $R_9$, $R_{10}$ and $R'_{10}$ each independently represent a hydrogen, an alkyl, an alkenyl, —$(CH_2)_m$—$R_{80}$, or $R_9$ and $R_{10}$ taken together with the N atom to which they are attached complete a heterocycle having from 4 to 8 atoms in the ring structure; $R_{80}$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_{80}$. Thus, the term "alkylamine" as used herein means an amine group, as defined above, having a substituted or unsubstituted alkyl attached thereto, i.e., at least one of $R_9$ and $R_{10}$ is an alkyl group. Amino groups with four hydrocarbon substituents that are positively charged are referred to as "ammonium" groups.

The term "acylamino" is art-recognized and refers to a moiety that can be represented by the general formula:

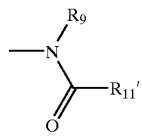

wherein R$_9$ is as defined above, and R'$_{11}$ represents a hydrogen, an alkyl, an alkenyl or —(CH$_2$)$_m$—R$_{80}$, where m and R$_{80}$ are as defined above.

The term "amido" is art-recognized as an amino-substituted carbonyl and includes a moiety that can be represented by the general formula:

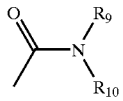

wherein R$_9$, R$_{10}$ are as defined above. In certain embodiments, the amide will include imides.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_{80}$, wherein m and R$_{80}$ are defined above. Representative alkylthio groups include methylthio, ethylthio, and the like.

The term "carbonyl" is art-recognized and includes such moieties as can be represented by the general formula:

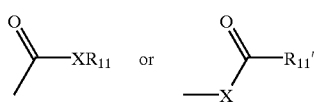

wherein X is a bond or represents an oxygen or a sulfur, and R$_{11}$ represents a hydrogen, an alkyl, an alkenyl, —(CH$_2$)$_m$—R$_{80}$ or a pharmaceutically acceptable salt, R'$_{11}$ represents a hydrogen, an alkyl, an alkenyl or —(CH$_2$)$_m$—R$_{80}$, where m and R$_{80}$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiocarbonyl" group. Where X is a sulfur and R$_{11}$ or R'$_{11}$ is not hydrogen, the formula represents a "thioester." Where X is a sulfur and R$_{11}$ is hydrogen, the formula represents a "thiocarboxylic acid." Where X is a sulfur and R$_{11}$' is hydrogen, the formula represents a "thioformate." On the other hand, where X is a bond, R$_{11}$ is not hydrogen, and the carbonyl is bound to a hydrocarbon, the above formula represents a "ketone" group. Where X is a bond, R$_{11}$ is hydrogen, and the carbonyl is bound to a hydrocarbon, the above formula represents an "aldehyde" group.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_{80}$, where m and R$_{80}$ are described above.

The term "sulfonamido" is art recognized and includes a moiety that can be represented by the general formula:

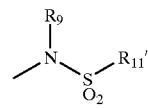

in which R$_9$ and R'$_{11}$ are as defined above.

The term "sulfoxido", as used herein, refers to a moiety that can be represented by the general formula:

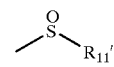

in which R'$_{11}$ is as defined above, but is not hydrogen.

A "sulfone", as used herein, refers to a moiety that can be represented by the general formula:

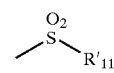

in which R'$_{11}$ is as defined above, but is not hydrogen.

The term "sulfamoyl" is art-recognized and includes a moiety that can be represented by the general formula:

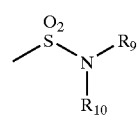

in which R$_9$ and R$_{10}$ are as defined above.

A "phosphoryl" can in general be represented by the formula:

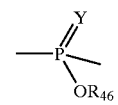

wherein Y represents O (or S, in the case of a thiophosphoryl), and R$_{46}$ represents hydrogen, a lower alkyl or an aryl. When used to substitute, e.g., an alkyl, the phosphoryl group of the phosphorylalkyl can be represented by the general formula:

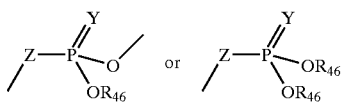

wherein Y represented S or O, and each R$_{46}$ independently represents hydrogen, a lower alkyl or an aryl, Z represents O, S or N. When Y is an S, the phosphoryl moiety is a "phosphorothioate".

A "phosphoramidate" can be represented in the general formula:

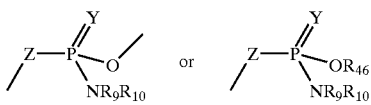

wherein $R_9$ and $R_{10}$ are as defined above, and Z represents O, S or N.

A "phosphonamidate" can be represented in the general formula:

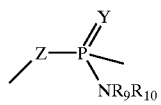

wherein $R_9$ and $R_{10}$ are as defined above, and Z represents O, S.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, hydrolysis, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991; and Kocienski, P. J. *Protecting Groups*, Georg Thieme Verlag: New York, 1994).

Description

Reactions of the present method involve the polymerization of substituted ethylene monomers in the presence of a reducing substrate (transfer agent), a peroxide source, and an enzyme. In certain embodiments, the reactions may be performed in the absence of oxygen, e.g., under an inert atmosphere, e.g., nitrogen or argon, or using degassed solvents. In certain embodiments, the reactions may be performed at ambient temperature.

Substitued ethylene monomers include compounds comprising a carbon-carbon double bond substituted by one or more organic substituents. For example, vinyl chloride, propylene, acrylic acid, methyl acrylate, acrylonitrile, methyl methacrylate, acrylamide, styrene, stilbene, cyclohexene, cyclopentene, and ethyl vinyl ether are all substituted ethylene monomers with respect to the present invention. Preferred substituted ethylene monomers are acrylic acid, acrylate esters, methacrylate esters, styrene, sodium acrylate, and acrylamide. In certain embodiments, the method may utilize more than one monomer for the synthesis of copolymers. In certain embodiments, the monomer may be an acrylic acid derivative of the general formula (I):

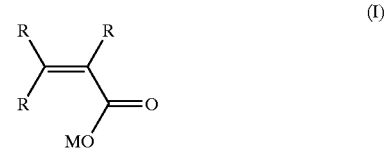

wherein
 M represents H, an alkali metal, an alkaline earth metal, or an ammonium counterion, and
 R represents, independently for each occurrence, H, a halogen, a ketone, an aldehyde, an ester, an amide, a carboxyl, a sulfonyl, a sulfoxide, an acylamino, a cyano, a lower alkyl group, a lower alkenyl group, a lower alkynyl group, or an aryl group.

Reducing substrates, also referred to herein as transfer agents, are compounds which promote the polymerization reaction, e.g., by serving as a ligand for a metal center in the enzyme or by transferring hydrogen atoms to free radicals in the radical chain mechanism. Preferred transfer agents are β-dicarbonyl compounds, such as malonic acid and derived esters, β-ketoesters, and β-diketones, especially 2,4-pentanedione. In certain embodiments, the reducing substrates may be represented by the formula:

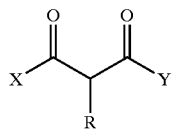

wherein
R, independently for each occurrence, represents H, a substituted or unsubstituted alkyl group, or a substituted or unsubstituted aryl or heteroaryl group;
X and Y, independently represent H, a substituted or unsubstituted alkyl group, a substituted or unsubstituted aryl or heteroaryl group, OR, $NH_2$, NHR, $NR_2$, SR, OH, or any two of X, Y, and R, taken together, comprising a ring of five to nine atoms, preferably five to seven atoms. Although a particular transfer agent may perform adequately in a wide range of reactions, in certain embodiments, it may be advantageous to determine the structure of the optimal transfer reagent for the particular substrate and reaction conditions.

A peroxide source useful in the present method may be any compound having an oxygen-oxygen bond, such as benzoyl peroxide, alkali and alkaline earth metal peroxides, mono- and dialkylperoxides, hydrogen peroxide bis-TMS ether, organic and inorganic peracids, or hydrogen peroxide. Reagents which generate a compound having an oxygen-oxygen bond under the reaction conditions are also peroxide sources as the term is used herein. Hydrogen peroxide is preferred because it generates only water as a byproduct.

The present method may employ any enzyme capable of catalyzing a polymerization in the presence of a peroxide source. Suitable enzymes include oxidases, such as xanthine oxidase and alcohol oxidase, peroxidases, such as soybean peroxidase, horseradish peroxidase, chloroperoxidase, related enzymes, or any other enzyme capable of reacting with a peroxide source. In certain embodiments, the enzyme is synthetic enzyme, preferably a modified enzyme, such as an enzyme synthesized using combinatorial mutagenesis. In certain embodiments, the enzyme is capable of existing at elevated temperatures, e.g., above 40° C., preferably above 60° C., even more preferably above 80° C., without being denatured or deactivated. Alternatively, an enzyme may be used which is capable of operating at lowered temperatures, e.g., below 20° C., preferably below 0° C., or even more preferably below –20° C. Enzymes capable of withstanding such elevated temperatures are referred to herein as thermophilic enzymes, those that operate at lowered temperatures are referred to herein as cryophilic enzymes, and those enzymes that operate at or around ambient temperature, e.g., between about 20° C. and about 40° C., are referred to herein as mesophilic.

The reactions may be performed in any solvent or mixture of solvents, whether or not the monomers used are soluble in the solvent or solvent mixture. Suitable solvents include dimethyl formamide (DMF), toluene, methylene chloride, dichloroethane, benzene, chlorobenzene, tetrahydrofuran (THF), ether, water, methanol, ethanol, propanol, butanol, butanone, acetone, dimethylsulfoxide (DMSO), nitromethane, dioxane, etc. In certain embodiments, the solvent mixture comprises water and a sufficient quantity of a water-miscible organic solvent, e.g., DMF, acetone, THF, DMSO, or dioxane, to solubilize the monomer(s).

In another embodiment, the reaction may be performed as a concentrated emulsion polymerization. The emulsion may be an inverse or 'oil-in-water' emulsion, in which an organic monomer forms an emulsion with an aqueous solvent, or a 'water-in-oil' emulsion, in which a charged or polar monomer forms an emulsion in a non-polar organic solvent. The latter type of emulsion may be referred to as an 'inverse emulsion'. For example, the hydrophilic monomer acrylamide may be dispersed in toluene for polymerization. A surfactant, such as sorbitane monooleate, may be added to the reaction. Suitable surfactants include any compounds having a charged or polar hydrophilic portion, and a non-polar or hydrophobic portion, such as alkyl sulfates, alkyl phosphates, alkyl carboxylates, alkyl ammoniums, alkyl sulfonates, polyethyleneglycol (PEG) derivatives, etc. A concentrated emulsion is a gel-like system whose internal phase ratio is greater than 0.74 (the volume fraction of the most compact arrangement of spheres of equal size). Compared to conventional inverse emulsion polymerization, a much smaller amount of organic solvent may be employed. In certain embodiments, performing a reaction in an emulsion may increase the rate of reaction.

In one embodiment, the reaction may be a partitioned polymerization. A partitioned polymerization, as the term is used herein, refers to a reaction wherein the enzyme is in one phase, e.g., the aqueous phase, and the monomer is in a different phase, e.g., the organic phase. For example, MMA may be polymerized in a partitioned polymerization. A surfactant, such as described above, may be added to the reaction mixture of a partitioned polymerization.

Polymers formed according to the present method may have properties difficult or impossible to obtain using conventional procedures. For example, the resultant polymer may be substantially stereoregular, e.g., greater than 70%, preferably greater than 85%, even more preferably greater than 90%, or most preferably greater than 95% syndiotactic or isotactic. In certain embodiments, the polymer may have a high number average molecular weight, e.g., greater than 5,000 amu, preferably greater than 7,500 amu, or even more preferably greater than 10,000 amu. In an embodiment of the present invention, the method is used to generate cross-linked polymers, such as, for example, polystyrene.

In certain embodiments, the yield of polymer produced in a reaction according to the present method is greater than 70%, preferably greater than 80%, even more preferably greater than 90%, or still more preferably greater than 95%.

III. Exemplification

Isolated peptidyl portions of enzymes useful in the present invention can be obtained by screening peptides recombinantly produced from the corresponding fragment of the nucleic acid encoding such enzymes. In addition, fragments can be chemically synthesized using techniques known in the art such as conventional Merrifield solid phase f-Moc or t-Boc chemistry. For example, an enzyme useful in the present method may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as polymerization catalysts.

The recombinant enzymes useful in the present invention also include homologs of the authentic enzymes, such as versions of those proteins which are resistant to thermal or chemical denaturation, for example, due to mutations which increase disulfide crosslinking in the enzyme. Enzymes useful in of the present invention may include proteins which have or have not been post-translationally modified in a manner different than the authentic protein.

Modification of the structure of the enzymes useful in the present method can be for such purposes as enhancing yield, stereoregularity of resultant polymers, or thermal or chemical stability of the enzyme. Such modified enzymes which retain the ability to catalyze the polymerization of substituted ethylene monomers are considered functional equivalents of the enzymes described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine, histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur -containing= cysteine and methionine. (see, for example, *Biochemistry*, 2nd ed., Ed. by L. Stryer, W H Freeman and Co.: 1981). Whether a change in the amino acid sequence of a peptide results in a functional homolog (e.g. functional in the sense that it catalyzes a polymerization reaction) can be readily determined by assessing the ability of the variant peptide to produce a polymer under standard polymerization conditions. Polypeptides in which more than one replacement has taken place can readily be tested in the same manner.

This invention further contemplates a method for generating sets of combinatorial mutants of the enzymes useful in the present invention as well as truncation mutants, and is especially useful for identifying potential variant sequences (e.g., homologs) that are functional in the present method. The purpose of screening such combinatorial libraries is to generate, for example, novel enzymes which can catalyze the polymerization reactions described herein. To illustrate, enzymes useful in the present invention can be engineered by this method to provide more efficient reactivity or improve the properties of the resulting polymer.

Enzymes or peptide fragments modified by combinatorial mutagenesis or other techniques may be tested for performance in the present method in any number of ways. For example, an assay may combinatorially test the engineered polypeptides in a polymerization reaction of a volatile monomer. After the reaction has proceeded, the solvent and residual monomer may be removed or allowed to evaporate leaving only polymer residue, which may be easily quantified to identify polypeptides which are active in the present method. Subsequent testing of active enzymes under particular conditions, e.g., elevated temperature, specific monomers, etc., may be used to identify enzymes with additional advantageous properties. Other suitable methods for screening engineered polypeptides of the present invention will be apparent to those of skill in the art.

In certain embodiments, it will be desirable to immobilize the enzyme, natural or modified, to facilitate separation of the enzyme from the reaction medium. In one embodiment, a fusion protein can be prepared which adds a domain that allows the protein to be bound to a matrix. For example, glutathione-S-transferase (GST) domains can be adsorbed onto glutathione sepharose beads (Sigma Chemical, St. Louis, Mo.) or glutathione derivatized microtitre plates.

Other techniques for immobilizing proteins on matrices are also available for use in the present method. For instance, soluble portions of an enzyme catalyst may be immobilized utilizing conjugation of biotin and streptavidin. For instance, biotinylated receptor molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemical).

Experimental Section

Instrumentation

Nuclear Magnetic Resonance (NMR). NMR data were recorded on Bruker DPX300, AMX500 and DMX400 equipped with a 10 mm broad end probe for obtaining $^{13}$C and Distortionless Enhancement by Polarization Transfer (DEPT) NMR spectra. The spectrometers were also equipped with a 5 mm inverse detection probe for obtaining $^{1}$H, pulsed-field gradient-filtered (PFG), COSY, HSQC, and HMBC spectra. $^{13}$C-NMR spectra were obtained using gated decoupling with an 8-second recycle delay between scans for 10,000 scans for quantitation of resonances. The DEPT spectra were obtained using a 500 ms recycle delay for ~3,000 scans. The $^{1}$H data were obtained using a 4-second recycle delay between scans. A PFG-filtered sample was obtained to remove the interference of small molecules from the spectra of the polymer.

Molecular Weight Measurements. The number average molecular weights (Mn) of the polymer samples were determined by gel permeation chromatography (GPC). GPC also allowed calculations of molecular weight distribution (Mw/Mn), where Mw is the weight average molecular weight. Studies by GPC were carried out using a Waters, Inc., a Model 410 refractive index detector, and a GMPWXI TOSOHAAS TSK-Gel column for water-soluble polymers and 2×PLGel 5 μm column for THF-soluble polymers. THF was used as the eluent for methyl methacrylate polymers at a flow rate of 1.0 mL/min at 40° C. Sodium dihydrogen phosphate, 20 mM, pH 7.0, was used as the eluent for water-soluble polymers at the rate of 1 mL/min at ambient temperatures. The injection volume used was 100 μL and 50 μL respectively for THF and water-soluble polymers. Polystyrene standards with a narrow polydispersity were used to generate a calibration curve for THF-soluble polymers. Polyacrylic acid standards with narrow polydispersity were used to generate a calibration curve for water-soluble polymers.

Thermal Analysis. Samples were heated to 150° C., cooled to 30° C. and then reheated to 150° C. The heating rate was 20° C./min and the purge gas was helium. The analysis method employed was the Tg midpoint, half-height method.

Synthetic Procedures

Horseradish peroxidase (Type II, activity 150–200 units/mg), hydrogen peroxide (30% w/v) were obtained from Sigma chemical company. Methanol, dioxane, acetone, tetrahydrofuran and dimethylformamide were of analytical grade and were used as received. Methyl methacrylate (MMA) obtained from Aldrich chemical company was fractionally distilled over calcium hydride under reduced pressure in a nitrogen atmosphere. 2,4-Pentanedione from Aldrich was distilled before using. Acrylamide, sodium acrylate, sorbitane monooleate obtained from Aldrich were used as received. Sodium lauryl sulfate was a gift from the Rohm and Haas company and was used as received. Other enzymes, including soybean peroxidase and microbial or fungal peroxidases can be used in place of horseradish peroxidase to carry out the same reactions. We anticipate that modifications to these enzymes may permit further control of the structural features of the polymers synthesized.

ENZYME-MEDIATED POLYMERIZATION OF ACRYLAMIDE IN AQUEOUS MEDIA

Acrylamide (1.46 mmol in 2 mL water) in a dual inlet ampule was purged with nitrogen for 10 min. Into the above solution, HRP (4 mg in 0.1 mL water), hydrogen peroxide (0.023 mmol) and 2,4-pentanedione (0.034 mmol) were successively injected while stirring. The reactions were carried out for a predetermined time period while maintaining both stirring and a nitrogen atmosphere. After the reaction, the reaction mixture was poured into an excess of methanol. The resulting precipitate was filtered off, washed with methanol and dried under vacuum at 50° C., 30 mm Hg for 24 hours.

ENZYME-CATALYZED POLYMERIZATION OF ACRYLAMIDE USING SORBITANE MONOOLEATE

Toluene (42 µL) and the surfactant, sorbitane monooleate (17.2 µL), were degassed in a dual inlet ampule for 10 min. Acrylamide (2.92 mmol) dissolved in water (0.45 mL) was added to the surfactant solution with stirring. To the above was added HRP (8 mg in 0.3 mL water), hydrogen peroxide (0.046 mmol), and 2,4-pentanedione (0.068 mmol) while vigorously stirring. The polymerization was carried out under a nitrogen stream for different time periods. The polyacrylamide was isolated by precipitation in acetone and then dried in a vacuum oven (50° C., 30 mm Hg, 24 hours).

ENZYME-CATALYZED STYRENE POLYMERIZATION

Styrene monomer (Aldrich) was purified by washing with 10% NaOH three times and then dried by $CaCl_2$ overnight. Generally, 5.52 mmol styrene, 700 µL $H_2O$, 300 µL THF, and 16 mg HRP (in 200 µL $H_2O$) solution were mixed under $N_2$, and 0.0918 mmol $H_2O_2$ and 0.137 mmol 2,4-pentanedione were then added simultaneously. Reactions ran for 24 hrs under $N_2$. The specific concentrations of reactants, reaction times, and other conditions were varied as described below.

After 24 h, the solution was poured into 250 ml MeOH to precipitate the polymer products. The MeOH solution was then vacuum filtered and washed five times with water. The solids were then dried 24 hrs in a vacuum desiccator to determine yields. For the reactions, styrene monomer was also purified by vacuum distillation at 8 mm Hg at 35° C., then dried by $CaCl_2$ with nitrogen and stored at −15° C. Note: controls for all reactions were run where individual components of the reaction mixture were omitted or the enzyme was heat-denatured by boiling.

RESULTS AND DISCUSSION

ENZYME-MEDIATED POLY(ACRYLAMIDE) SYNTHESIS

The polymerization in water of acrylamide catalyzed by HRP in the presence of hydrogen peroxide and 2,4-pentanedione provides poly(acrylamide) in yields of up to 98% within 3 hours (Table I). Measurements by GPC showed that the number average molecular weight ($M_n$) of the poly(acrylamide) products ranged between approximately 3,000 and 8,000 g/moles. $^{13}$C-NMR showed that the polymer is atactic. The microtacticity using Cα(CH) gave syndio- (rr=36%), hetero- (mr or rm=46%) and isotactic (mm=18%) triads (FIG. 1). The polymerization of acrylamide was more rapid when conducted within a concentrated emulsion using sorbitane monooleate as the surfactant as opposed to a water medium (nearly quantitative polymer formation within 1.25 and 3 hours, respectively). The molecular weight of the polyacrylamide obtained by using a concentrated emulsion was smaller than that synthesized in the aqueous medium (Table II). It may be that the transfer of a hydrogen radical from the surfactant hydrophilic headgroup to the propagating chain end results in higher rates of chain termination and, consequently, lower molecular weights than the reactions conducted in the aqueous medium. The microtacticity of the poly(acrylamide) in inverse emulsion gave syndio- (rr=3%), hetero- (mr or rm=45%) and isotactic- (mm=25%) triads.

ENZYME-CATALYZED POLYMERIZATION OF METHYL METHACRYLATE IN BINARY SOLVENT

Methyl methacrylate (MMA) (5.60 mmol) was added to a solution of distilled water (0.7 mL) and organic solvent (0.3 mL) in a dual inlet ampule under nitrogen atmosphere. Horseradish peroxidase in 0.2 mL water (80 mg/mL, 16 mg of enzyme), hydrogen peroxide (0.092 mmol), and 2,4-pentanedione (0.136 mmol) were successively injected while stirring. The reaction mixture was maintained under nitrogen with stirring at room temperature for a predetermined time period. Then, the reaction mixture was poured into a large excess of methanol. The precipitate obtained was filtered off, washed with methanol and dried under vacuum at 50° C., 30 mm Hg for 24 hours.

PARTITION EMULSION POLYMERIZATION OF METHYL METHACRYLATE CATALYZED BY HORSE RADISH PEROXIDASE USING SODIUM LAURYL SULFATE AS THE SURFACTANT

Methyl methacrylate (4.27 mmol) was added to a water solution (0.5 mL) of SDS ($10^{-4}$ mol/L, 28%) with vigorous stirring under nitrogen atmosphere. HRP solution (10.8 mg in 0.3 mL water), hydrogen peroxide (0.061 mmol), and 2,4-pentanedione (0.092 mmol) were successively injected into the above solution while stirring. The polymer yield was measured gravimetrically after the product was precipitated into an excess of methanol. The precipitated polymer was separated, washed with methanol, water, dried in a vacuum oven (50° C., 30 mm Hg) and weighed.

POLY(METHYL METHACRYLATE)—RESULTS AND DISCUSSION

The room temperature polymerization of methyl methacrylate (MMA) catalyzed by HRP in the presence of hydrogen peroxide and 2,4-pentanedione was carried out in binary solvent mixtures consisting of water and different co-solvents. The polymer formed, based on analyses by high field proton NMR, was predominantly syndiotactic. When the binary mixture was water:DMF (3:1), the polymerization was very slow (<5% monomer conversion in 24 h). The low yields in water/DMF is presumably due to unfavorable interactions between HRP and DMF resulting in enzyme deactivation. The yields of PMMA increased when less polar solvents were used. Specifically, for 24 h polymerizations in water/acetone, water/dioxane and water/THF (all 3:1 v/v), the PMMA yields were 8, 45 and 90%, respectively.

Figure 3:
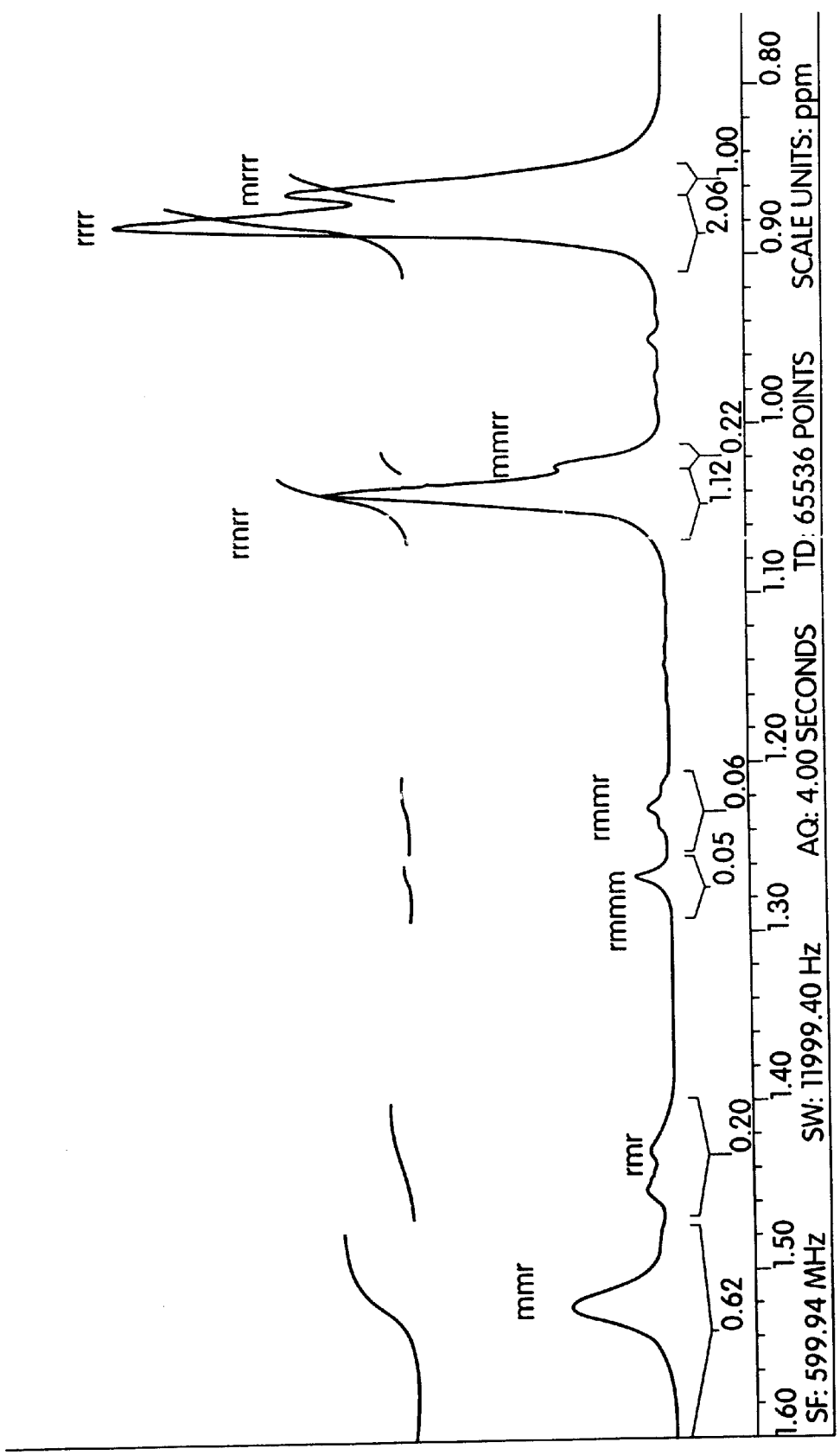
FIG. 3 is a plot of the expanded methyl pentad sequence of the spectrum of PMMA of FIG. 2 prepared by a method described herein.
Figure 4:
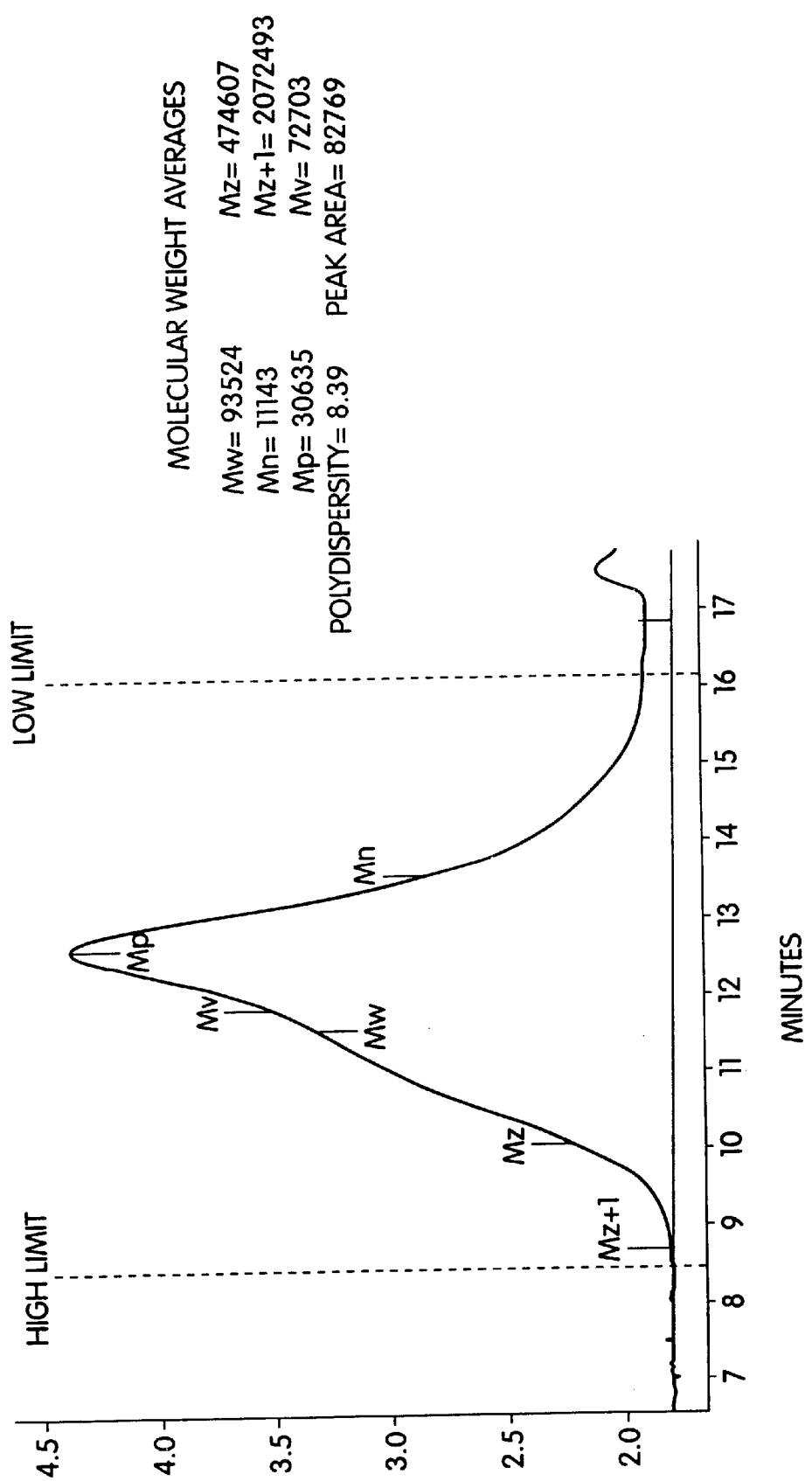
FIG. 4 is a GPC profile of PMMA in THF prepared by a method described herein.
Figure 5:
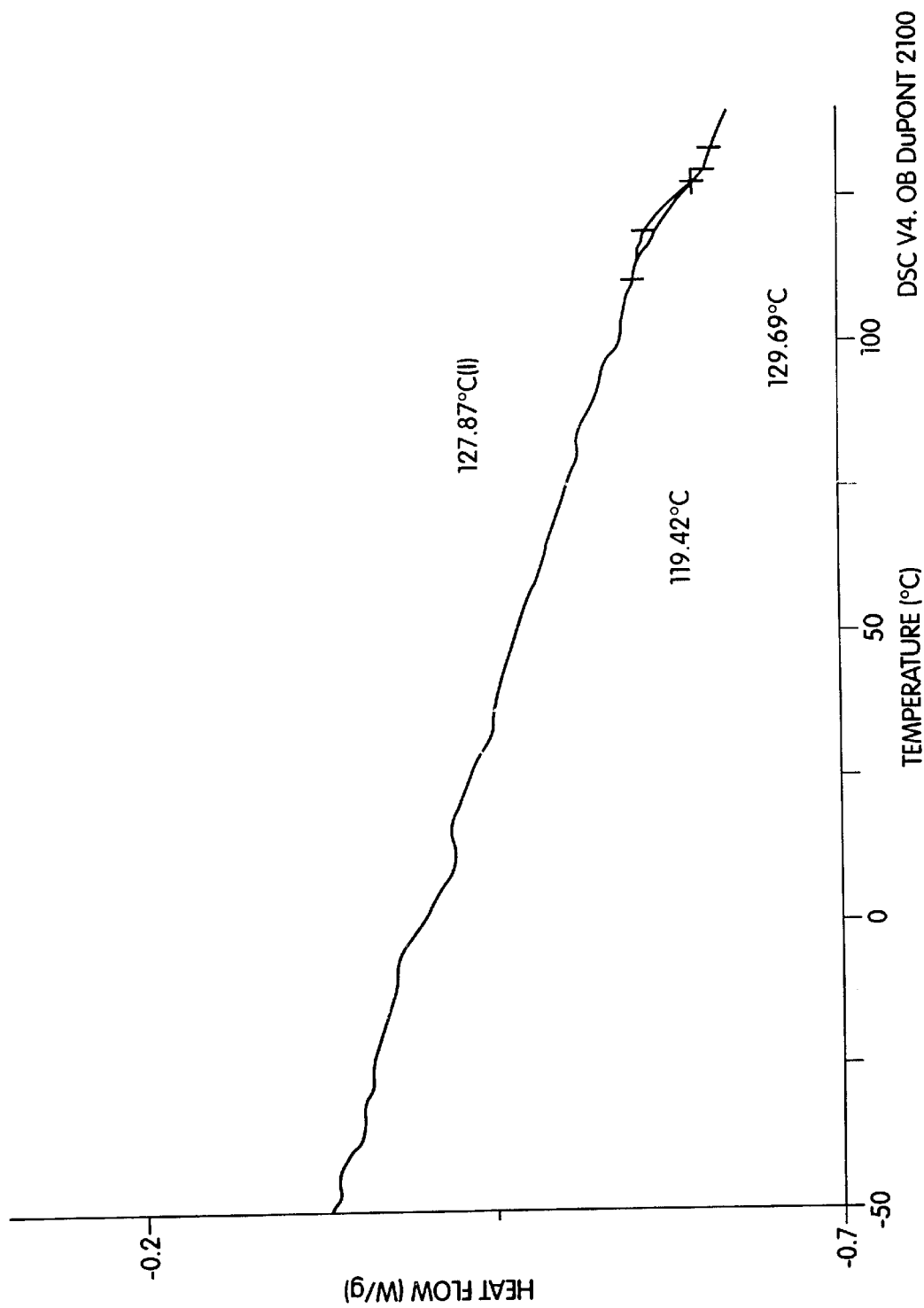
FIG. 5 is a DSC thermogram of a predominantly syndiotactic PMMA prepared by this invention.
Figure 6:
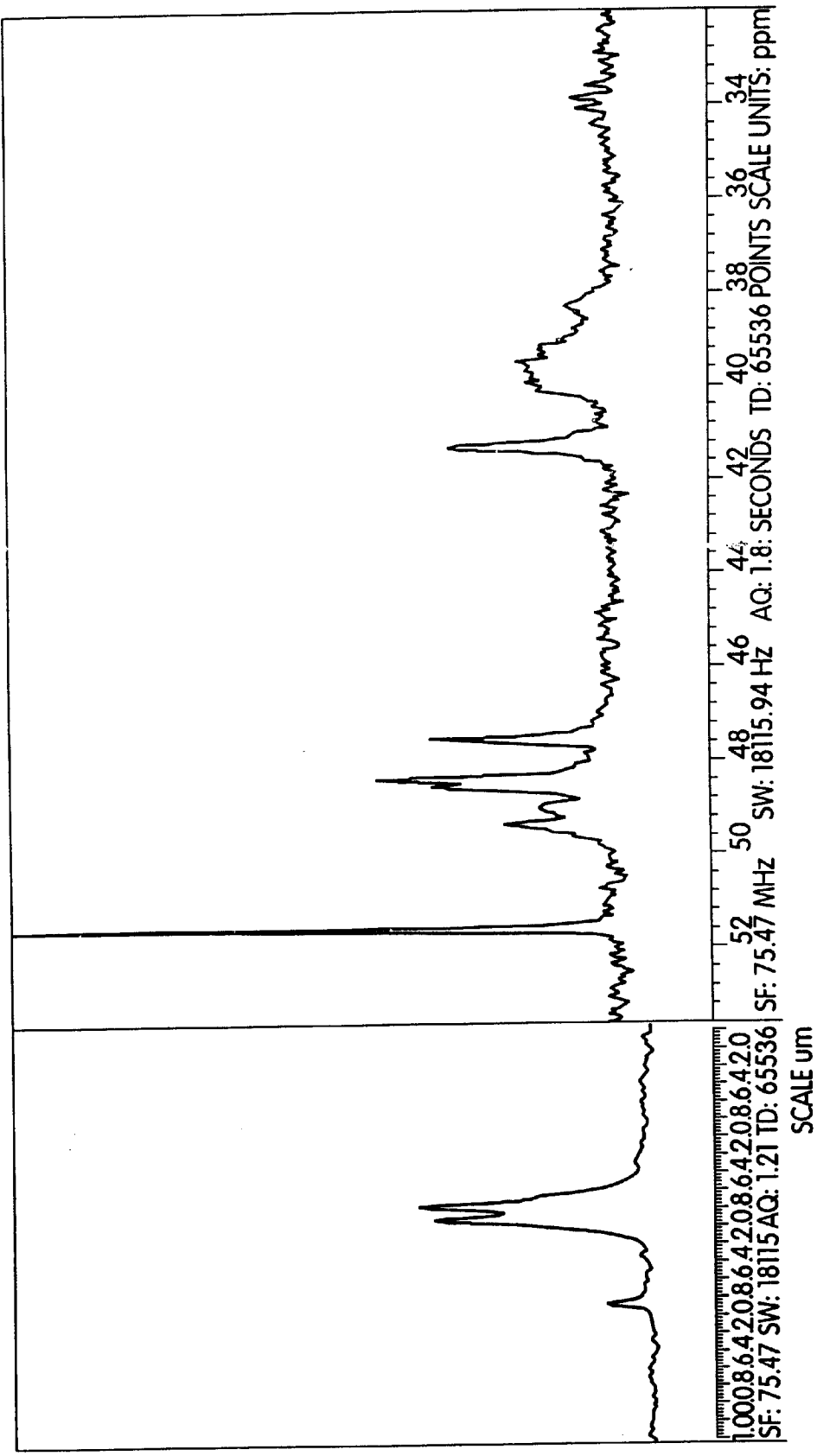
FIG. 6 is a $^{13}$C-NMR spectrum of poly(sodium acrylate) in D$_2$) prepared by a method described herein.
Figure 7:
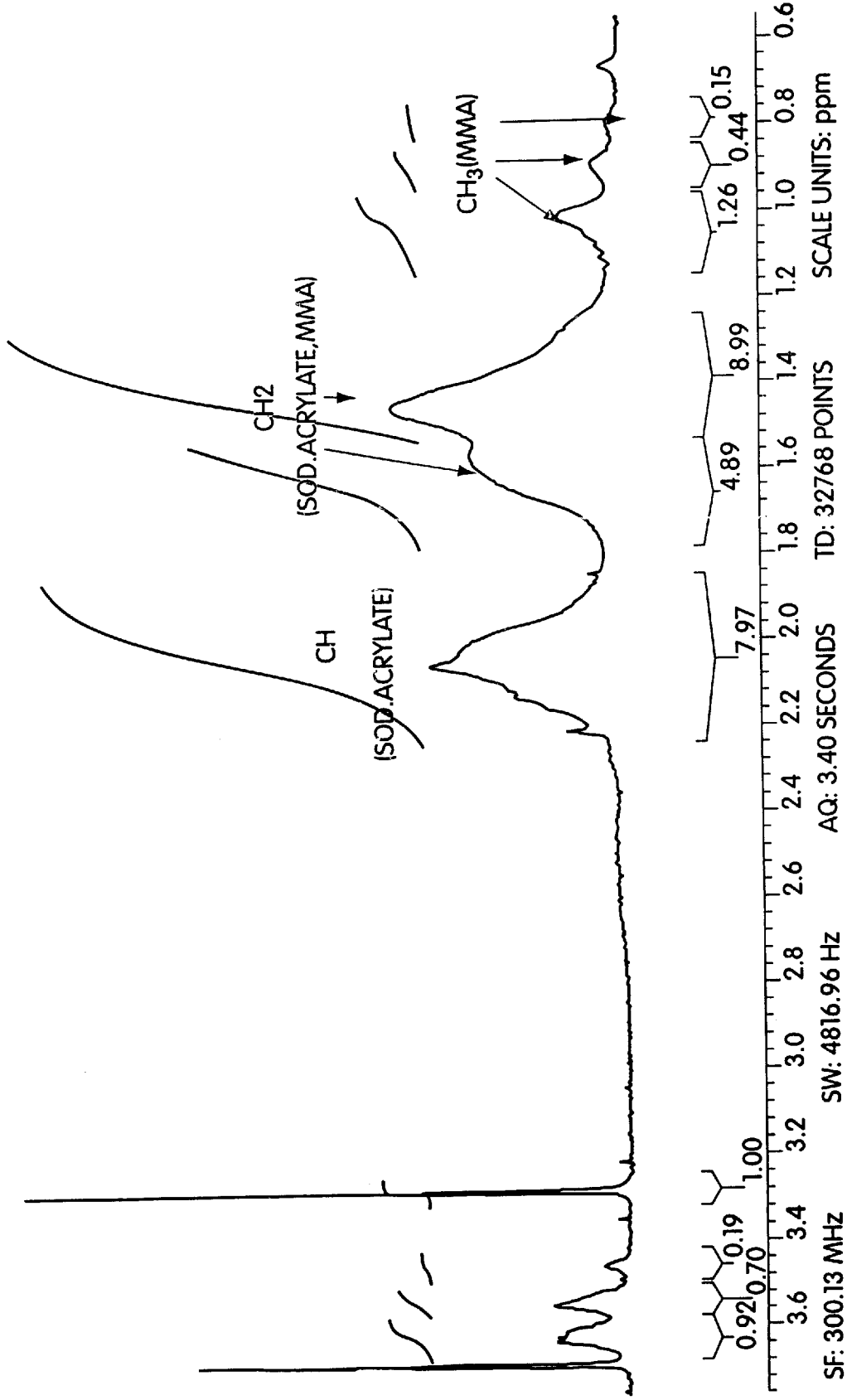
FIG. 7 is an APT spectrum of a copolymer of MMA and sodium acrylate (1:9 wt %) prepared by the present method.

The water:dioxane (3:1 v/v) reaction medium was found to be the best solvent system of those studied for syndio-regulation (see Table III). In other words, study of the repeat unit sequence distribution for MMA polymerization using HRP as the catalyst showed that the syndiotacticity of the product was highest when conducting the polymerization in water:dioxane (3:1 v/v). Increasing the ratio of dioxane to water resulted in decreased polymer yield and increased syndiotacticity (Table III). Analysis of the syndio-PMMA products by GPC established that they were of high molecular weight ($M_n$ between 7,000 and 24,000 g/mole). Measurements by DSC confirmed that PMMA products of high syndiotacticity (about 85% based on analysis of pentad sequences, FIG. 3) had glass transition temperatures of about 131° C. (FIG. 4)

Increase of the MMA polymerization temperature to 34° C. resulted in a decrease in the polymer yield as well as the degree of syndiotacticity (Table IV). A study of how variations of the HRP and 2,4-pentanedione concentration effect the outcome of MMA (5.6 mmoles) polymerizations showed that 16 mg of enzyme and 1.36 mmol of 2,4-pentanedione were preferred for enhancing chain syndioregularity (see Tables V and VIA). The partition polymerization of MMA was also studied at room temperature using the preferred HRP: 2,4-pentadione:MMA stoicheometry determined above. It was found that for the same reaction periods, the emulsion polymerization using sodium lauryl sulfate as the surfactant gave higher PMMA yields than the corresponding polymerization of MMA in water:dioxane (Table VII). Furthermore, the GPC analysis gave high number average molecular weights ($M_n$) of about 40,000 and above with low polydispersities of PMMA in sodium lauryl sulfate.

POLYMERIZATION OF ACRYLAMIDE AND METHYL METHACRYLATE IN WATER-DIOXANE SYSTEM

Variable ratios of acrylamide and methyl methacrylate were added to water:dioxane (2.5:1, 1.4 mL total) so that the total monomer content was 7 mmoles. The solution was purged with nitrogen for 10 min. HRP (19 mg in 0.2 mL water), hydrogen peroxide (0.11 mmol) and 2,4-pentanedione (0.1632 mmol) were successively injected into the monomer solution with stirring. The stirring was continued for 24 hours under nitrogen atmosphere. After 24 h, the reaction mixture was poured into an excess of methanol. The precipitate obtained was filtered and dried under vacuum (50° C., 30 mm Hg, 24 h).

ENZYME-MEDIATED COPOLYMERIZATION OF ACRYLAMIDE AND METHYL METHACRYLATE USING SODIUM LAURYL SULFATE

To a water solution (1.0 mL) containing SDS ($10^{-4}$ mol/L, 28%), a mixture of acrylamide and MMA were added in predetermined ratios (total monomer, 8 mmol) and the solution was stirred under nitrogen for 10 min. HRP (21.6 mg in 0.6 mL water), hydrogen peroxide (0.16 mmol), and 2,4-pentanedione (0.85 mmol) were successively injected under a nitrogen stream to the emulsion. The polymerization was continued for 24 hrs under a nitrogen atmosphere with vigorous stirring. After 24 hrs, the reaction mixture was poured into an excess of methanol, filtered, and dried under vacuum (50° C., 30 mm Hg) for 24 hours.

ENZYME-MEDIATED POLYMERIZATION OF SODIUM ACRYLATE IN AQUEOUS MEDIUM

A solution of sodium acrylate (4 mmol) in distilled water (1.5 mL) was purged with nitrogen for 10 min. HRP (11.4 mg in 0.5 mL water), hydrogen peroxide (0.064 mmol) and 2,4-pentanedione (0.097 mmol) were successively injected under nitrogen atmosphere with vigorous stirring. The polymerization was continued with stirring for the stated time periods. The reaction mixture was then poured into an excess of methanol. The precipitate obtained was filtered and dried under vacuum at 50° C. to yield the product.

ENZYME-MEDIATED COPOLYMERIZATION OF METHYL METHACRYLATE AND SODIUM ACRYLATE IN WATER-DIOXANE SYSTEM

Variable ratios of MMA and sodium acrylate were added to a solution of water (1.5 mL) and dioxane (0.8 mL) so that the total monomer content was 6 mmol. The solution was purged with nitrogen gas for 10 min. HRP (16 mg in 0.5 mL of water), hydrogen peroxide (0.092 mmol), and 2,4-pentanedione (0.136 mmol) were successively injected into the monomer solution with stirring. The stirring was continued for 24 h under nitrogen atmosphere, then the reaction mixture was poured into an excess of methanol. The precipitate obtained was filtered, dried under vacuum (50° C., 30 mm Hg) to yield the copolymer.

POLYMERIZATION OF METHYL METHYLACRYLATE (MMA) USING INITIATOR DIBENZOYLACETONE

Figure 9:
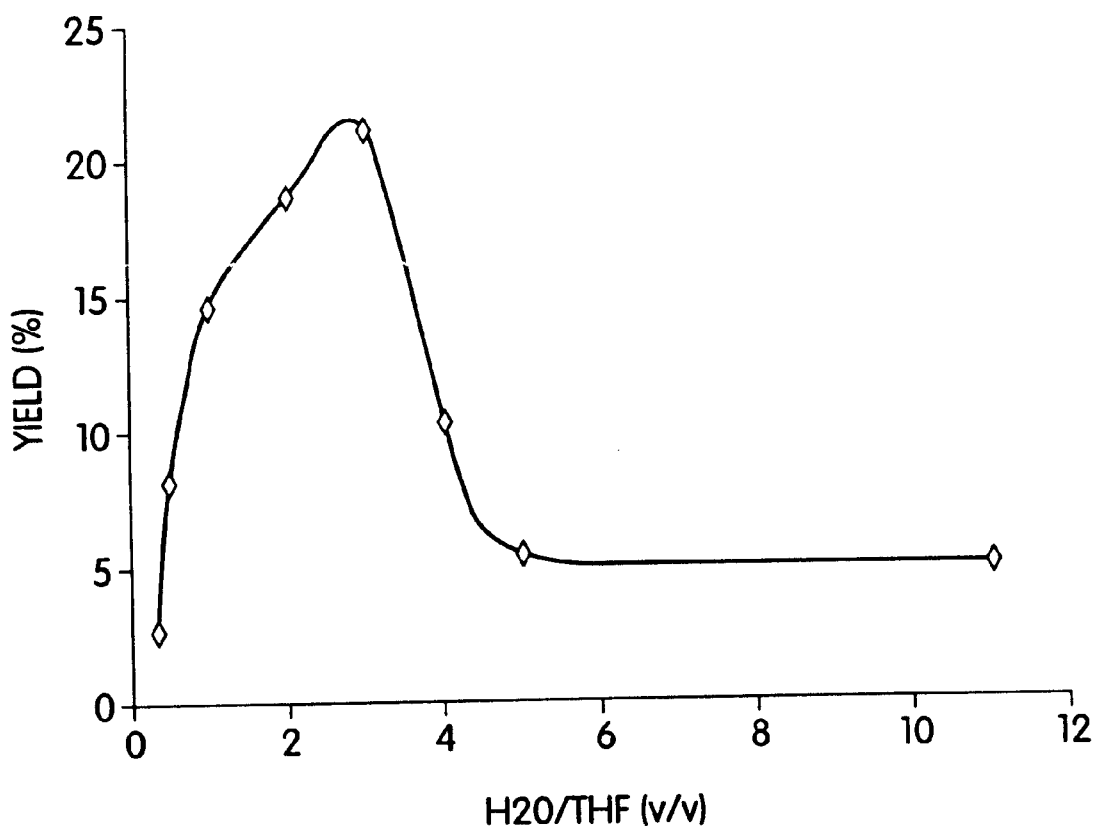
FIG. 9 presents results for the use of a variety of transfer agents in MMA polymerizations.

Methyl methylacrylate (MMA) (5.56 mmol, 560 μL) was added to a solution of distilled water (700 μL) and tetrahydrofuran (300 μL) in a round bottom flask under nitrogen atmosphere. Horseradish peroxidase in a 200 μL water (16 mg) hydrogen peroxide (0.92 mmol) and dibenzoylacetone (0.092 mmol) were successively injected while stirring. The reaction mixture was maintained under nitrogen atmosphere with stirring at room temperature for a predetermined time period. The reaction mixture was poured into a large excess of methanol. The precipitate was filtered off, washed with methanol, then with water and dried. Four more experiments were carried out by only changing the amount of initiator ie 0.276 mmol, 0.552 mmol, 0.828 mmol and 1.104 mmol. Results are presented in Table VIB. Results for polymerizations employing other transfer agents are presented in FIG. 9.

TABLE I

| TIME (IN MIN.) | % ISOLATED YIELD | Mn | Mw/Mn |
|---|---|---|---|
| 30 | — | — | — |
| 45 | — | — | — |
| 60 | 1.9 | N.D. | N.D. |
| 90 | 24.13 | 1200 | 12.2 |
| 120 | 71.5 | 3315 | 14.0 |
| 150 | 82.6 | 2994 | 16.0 |
| 180 | 98.0 | 7879 | 23.0 |

TABLE II

| TIME (IN MIN.) | % YIELD | Mn | Mw/Mn |
|---|---|---|---|
| 30 | 9.6 | 1200 | 112.5 |
| 45 | 84.7 | 5400 | 28.9 |
| 60 | 86.9 | 1800 | 45.6 |
| 85 | 98.8 | 1800 | 39.4 |

TABLE III

| COSOLVENT | % YIELD | Mn | Mw/Mn | Tg(° C.) | Syn-dyad |
|---|---|---|---|---|---|
| 25% DMF | <2.0 | N.D. | N.D. | N.D. | N.D. |
| 25% Acetone | 7.0 | 17953 | 6.7 | 128 | 0.854 |
| 25% Dioxane | 44.8 | 11143 | 8.4 | 131 | 0.86 |
| 50% Dioxane | 38.0 | 9756 | 6.8 | 126 | 0.86 |
| 75% Dioxane | 7.0 | 22956 | 4.3 | N.D. | 0.848 |
| 25% THF | 85.0 | 23676 | 14.4 | 128 | 0.841 |

TABLE IV

| TIME (IN HRS) | % YIELD | Mn | Mw/Mn | Tg | Syn-dyad |
|---|---|---|---|---|---|
| 2 | 5.1 | 8084 | 8.3 | 117 | 0.82 |
| 4 | 12.5 | 22146 | 28.3 | 112 | 0.82 |
| 6 | 17.4 | 16264 | 6.3 | 116 | 0.846 |
| 8 | 26.0 | 10467 | 10.0 | 107 | 0.863 |
| 16.5 | 34.5 | 10149 | 9.0 | N.D. | 0.83 |
| 24.0 | 44.8 | 11143 | 8.4 | 131 | 0.860 |
| 24.0* | 36.0 | 15414 | 10.2 | 127 | 0.830 |

*Reaction at 34° C.

TABLE V

| HRP (in mgs) | % YIELD | Mw/Mn | Syn-dyad |
|---|---|---|---|
| 14 | 38.7 | 13.6 | 0.839 |
| 16 | 45.1 | 8.4 | 0.860 |
| 18 | 56.1 | 9.9 | 0.846 |

TABLE VIA

| 2,4-Pentanedione (in mmoles) | % YIELD | Mw/Mn | Syn-dyad |
|---|---|---|---|
| 0.097 | 17.6 | 58.0 | 0.837 |
| 0.116 | 88.0 | 13.3 | 0.807 |
| 0.136 | 45.0 | 8.4 | 0.860 |
| 0.155 | 13.6 | 6.8 | 0.837 |

TABLE VIB

| Benzoyl Acetophenone | H₂O₂ (mmol) | Polymer Yield (%) |
|---|---|---|
| 0.092 | 0.092 | 1.4 |
| 0.276 | 0.092 | 0.8 |
| .0552 | 0.092 | 4.5 |
| 0.828 | 0.092 | 14.6 |
| 1.104 | 0.092 | 10.0 |

TABLE VII

| TIME (IN HRS) | % YIELD | Mn | Mw/Mn | Syn-dyad |
|---|---|---|---|---|
| 2 | 44.8 | 45000 | 6.6 | 0.846 |
| 4 | 52.9 | 40000 | 5.2 | 0.850 |
| 6 | 63.3 | 42000 | 6.5 | 0.849 |
| 8 | 68.6 | 49000 | 5.8 | 0.841 |
| 24 | 76.6 | 49000 | 4.3 | 0.832 |

TABLE VIII

| fmma/fac | % Yield | Mn | Mw/Mn | Fmma/Fac |
|---|---|---|---|---|
| 75/25 | 39.3 | N.D.* | N.D.* | N.D.* |
| 50/50 | 60.2 | N.D.* | N.D.* | N.D.* |
| 25/75 | 59.8 | N.D.* | N.D.* | N.D.* |

*copolymer insoluble in water, acetone, DMSO, THF, chloroform, dioxane, toluene, acetonitrile

TABLE IX

| TIME (IN HRS) | % YIELD | Mn | Mw/Mn |
|---|---|---|---|
| 2 | 38.0 | 600 | 17.0 |
| 4 | 43.6 | 14000 | 13.7 |
| 6 | 49.0 | 13000 | 14.9 |
| 8 | 79.0 | 13000 | 14.7 |
| 16 | 84.5 | 16000 | 12.9 |
| 24 | 87.2 | 11000 | 15.3 |

TABLE X

| fmma/fsod.ac | % Yield | Mn | Mw/Mn | Fmma/Fsod.ac |
|---|---|---|---|---|
| 90/10 | 28.4 | N.D.* | N.D.* | N.D.* |
| 75/25 | 50.2 | N.D.* | N.D.* | N.D.* |
| 50/50 | 54.8 | 8500 | 6.9 | |
| 25/75 | 48.4 | 1500 | 7.9 | 19/81 |
| 10/90 | 28.6 | 1200 | 9.3 | 13/87 |

*copolymer insoluble in water, acetone, DMSO, THF, chloroform, dioxane, toluene, acetonitrile

RESULTS OF STYRENE POLYMERIZATIONS

General procedure for polymerization

At room temperature, 700 µL water and 300 µL tetrahydrofuran were mixed and the flask was flushed with nitrogen for 15 minutes. 687 µL styrene monomer (6.0 mmol) was then added and reaction mixture was further flushed with nitrogen. 16 mg horseradish peroxidase ($3.56 \times 10^{-4}$ mmol, 2400 units) was completely dissolved in 200 µL water and added into the reaction mixture. 13.6 µL $H_2O_2$ (0.12 mmol) and 0.12 mmol of initiator (26.9 mg dibenzoylmethane, 12 mg tetronic acid, 19.4 mg 4-hydroxycoumarin, 19.5 mg 1-benzoylacetophenone, or 11.7 mg 1,3-cyclopentanedione) were added together after addition of enzyme. Polymerization was continued at room temperature for 48 hours with continuous stirring. The reaction mixture was poured into 300 mL of methanol after polymerization. After 24 hours, the mixture was filtered and the residue was washed with water five times and dried.

Initial Control Experiments

Polymerizations were performed according to the standard protocol, omitting one or more reagents as indicated by Table XI below.

TABLE XI

| Sample | Styrene | THF | $H_2O$ | HRP | $H_2O_2$ | 2,4 Pentanedione | Result |
|---|---|---|---|---|---|---|---|
| 1 | * | * | * |   |   |   | N |
| 2 | * | * | * | * |   |   | N |
| 3 | * | * | * |   | * |   | N |
| 4 | * | * | * |   |   | * | N |
| 5 | * | * | * |   | * | * | N |
| 6 | * | * | * | * |   | * | N |
| 7 | * | * | * | * | * |   | N |
| 8 | * | * | * | * | * | * | Y |

Effect of Reaction Time and $H_2O_2$ concentration on Styrene Polymerization

Figure 8A:
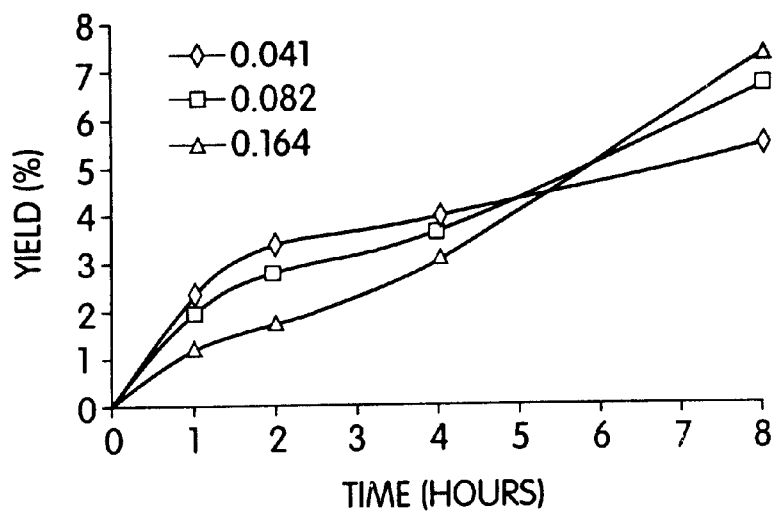
FIG. 8 depicts the kinetic profile of styrene polymerizations using varying amounts of peroxide.
Figure 8B:
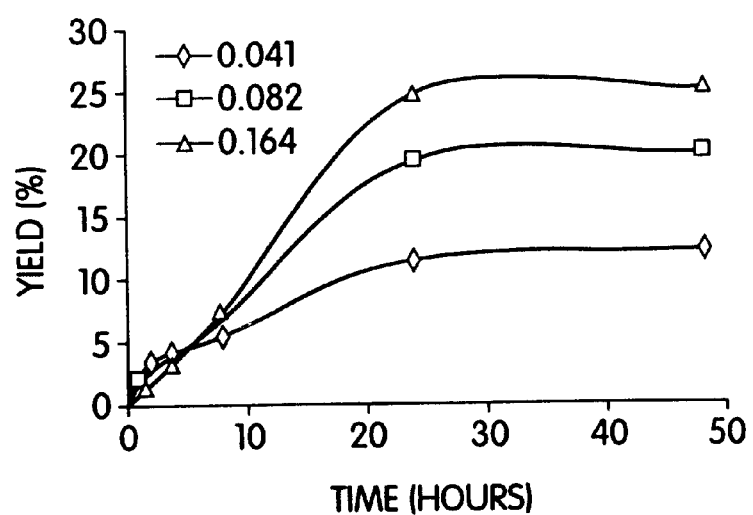

Conditions: 4.6 M styrene, 0.082 M 2,4-pentadione, $3 \times 10^{-4}$ M HRP, and 0.041, 0.082, or 0.164 M $H_2O_2$ in 300 µL THF and 900 µl $H_2O$. The initial polymerization rate increases with decreasing peroxide concentration (FIG. 8A). However, the rate and yield benefit from higher peroxide concentration over longer periods of time (FIG. 8B). Table XII shows the effect of reaction time on polydispersity.

TABLE XII

| Reaction Time (hrs) | Mn | Mw | Polydispersity |
|---|---|---|---|
| 0 | 0 | 0 | — |
| 4 | 11,903 | 16,830 | 1.41 |
| 8 | 23,520 | 74,134 | 3.15 |
| 24 | 31,799 | 104,800 | 3.12 |

Effect of Organic Solvent on Styrene Polymerization

Conditions—4.6 M styrene, 0.082 M 2,4-pentadione, 2667 units/mL HRP, and 0.077 M $H_2O_2$ in 300 µl organic solvent and 900 µL $H_2O$. Results are depicted in Table XIII.

TABLE XIII

| Solvent | THF | Dioxane | DMF | Methanol | $H_2O$ |
|---|---|---|---|---|---|
| Yield (%) | 21.2 | 4.2 | 4.2 | 3.8 | 3.2 |
| Mn | 31,799 | 41,210 | 10,896 | 13,848 | 13,547 |
| Mw | 104,800 | 132,859 | 13,895 | 36,357 | 29,449 |
| r | 3.12 | 1.28 | 1.28 | 2.63 | 2.17 |

Effect of Water/THF Ratio on Styrene Polymerization

Conditions—4.6 M styrene, 0.082 M 2,4-pentadione, 2667 units/mL HRP, and 0.082 M $H_2O_2$ in 1.2 mL of aqueous THF. Results are presented in Table XIV. $\infty$ represents pure water.

TABLE XIV

| $H_2O$/THF | $\infty$ | 11.00 | 5.00 | 4.00 | 3.00 | 2.00 | 1.00 | 0.50 | 0.33 |
|---|---|---|---|---|---|---|---|---|---|
| Yield (%) | 3.2 | 5.0 | 5.4 | 10.4 | 21.0 | 18.6 | 14.7 | 8.4 | 2.9 |
| Mn | 13,547 | — | 12,622 | 27,820 | 31,799 | — | — | — | — |
| Mw | 29,499 | — | 21,315 | 57,431 | 104,800 | — | — | — | — |
| r | 2.17 | — | 1.69 | 2.06 | 3.12 | — | — | — | — |

Effect of 2,4-Pentanedione Concentration on Styrene Polymerization

Conditions—4.6 M styrene, x M 2,4-pentadione, 2667 units/mL HRP, and 0.077 M $H_2O_2$ in 300 µL THF and 900 µL $H_2O$. Results are presented in Table XV.

TABLE XV

| 2,4-pentanedione (mol/l) | 0.131 | 0.114 | 0.098 | 0.082 | 0.058 | 0.041 | 0.017 |
|---|---|---|---|---|---|---|---|
| Yield (%) | 1.0 | 4.0 | 14.6 | 22.3 | 9.9 | 3.0 | 1.0 |
| Mn | — | — | 23,464 | 29,863 | — | — | — |
| Mw | — | — | 52,291 | 63,686 | — | — | — |
| r | — | — | 2.23 | 2.13 | — | — | — |

Effect of Reactant Addition

HRP-mediated polymerization of styrene was studied to determine the effect of the manner of addition of hydrogen peroxide on the yield of the reaction. As shown in Tables XVA and B, multiple additions of peroxide, adding quantities of differing amounts, dramatically increase the yield.

Conditions for Table XVA—4.6 M styrene, 0.082 M 2,4-pentadione, and 2667 units/mL HRP in 300 µL THF and 900 µL $H_2O$, with amounts of peroxide added successively to sum a total amount.

TABLE XVA

| | Addition Times | | | | | |
|---|---|---|---|---|---|---|
| Total [$H_2O_2$] | 0 | 1 | 2 | 5 | 8 | 10 |
| 0.041 | 0.0 | 13.3 | 19.7 | 19.9 | 30.8 | 39.6 |
| 0.082 | 0.0 | 19.8 | 23.3 | 25.4 | 34.8 | 42 |
| 0.164 | 0.0 | 22.5 | 25.7 | 28.5 | 35.2 | 43.3 |
| 4.6 | 0.0 | 0.0 | 0.0 | 0.0 | 0.0 | 0.0 |

Conditions for Table XVB—4.6 M styrene, 0.082 M 2,4-pentadione, 2667 units/mL HRP, and 0.1064 M total $H_2O_2$ in 300 µL THF and 900 µL $H_2O$, the peroxide being added gradually to achieve the given concentration (assuming non-consumption of peroxide).

TABLE XVB

| Times | 0 | 1 | 2 | 5 | 8 | 10 | 20 | 30 |
|---|---|---|---|---|---|---|---|---|
| Yield (%) | 0 | 22.5 | 25.7 | 28.5 | 36.8 | 43.3 | 42.5 | 41.3 |
| Mn | — | 15,632 | — | 15,449 | — | 65,182 | — | — |
| Mw | — | 28,260 | — | 39,489 | — | 170,299 | — | — |
| r | — | 1.81 | — | 2.56 | — | 2.61 | — | — |

Effect of [2,4-PD]/[$H_2O_2$] Ratio

Conditions—4.6 M styrene, 0.082 M 2,4-pentadione, 2667 units/mL HRP, and 0.164, 0.082, 0.041, or 0.020 M $H_2O_2$ in 300 µL THF and 900 µL $H_2O$. The results are presented in Table XVII.

TABLE XVII

| RH (mol/L) | 0.041 | 0.082 | 0.082 | 0.082 | 0.082 |
|---|---|---|---|---|---|
| $H_2O_2$ (mol/L) | 0.164 | 0.164 | 0.082 | 0.041 | 0.021 |
| Ratio (RH/$H_2O_2$) | 1:4 | 1:2 | 1:1 | 2:1 | 4:1 |
| Yield (%) | 11.8 | 24.7 | 19.8 | 12.9 | 2 |
| Mn | — | 31,799 | 15,632 | 22,891 | — |
| Mw | — | 104,800 | 28,260 | 53,427 | — |
| r | — | 3.12 | 1.81 | 2.33 | — |

Effect of Multiple RH Additions

Conditions—4.6 M styrene, and 2667 units/mL HRP in 300 μL THF and 900 μL $H_2O$. Results are presented in Table XVIII.

TABLE XVIII

| | Additions (times) | | |
|---|---|---|---|
| RH | 1 | 1 | 6 |
| $H_2O_2$ | 1 | 10 | 6 |
| Yield (%) | 20.5 | 38.9 | 22.6 |
| Mn | 15,632 | 65,182 | 23,879 |
| Mw | 28,260 | 170,299 | 50,411 |
| r | 1.81 | 2.61 | 2.11 |

Effect of Enzyme Concentration

Conditions—4.6 M styrene, 0.082 M 2,4-pentadione, x M HRP, and 0.077 M $H_2O_2$ in 300 μL THF and 900 μL $H_2O$. Results are shown in the Table XIX.

TABLE XIX

| HRP (×$10^4$ mol/l) | 1.1 | 1.9 | 3.0 | 3.7 | 4.6 |
|---|---|---|---|---|---|
| Polystyrene Yield (%) | 7.4 | 12.5 | 20.4 | 24 | 25.8 |

Effect of Enzyme Catalyst

A variety of different peroxidases were tested in the polymerization reaction. Results are presented in Table XX.

TABLE XX

| Enzyme | Units (purpurogallin) | Yield (%) | Mn | Mw | r |
|---|---|---|---|---|---|
| Horseradish Peroxidase | 4800 | 20.5 | 31,799 | 104,800 | 3.12 |
| Soybean Peroxidase | 4800 | 24.5 | 40,617 | 116,964 | 2.88 |
| *Arthromyces ramosus* Perxidase | 450 | 1.4 | | | |
| Lactoperoxidase | 440 | 0.7 | | | |

Effect of Polymerization Temperature

Conditions—4.6 M styrene, 0.082 M 2,4-pentadione, 2667 units/mL HRP, and 0.082 or 0.164 M $H_2O_2$ in 300 μL THF and 900 μL $H_2O$. Results are presented in Table XXI and Table XXII for the two concentrations of $H_2O_2$ respectively. For Table XXII, the peroxide was added ten times at 15 min. intervals.

TABLE XXI

| Temperature (° C.) | 22 | 30 | 35 | 40 | 50 |
|---|---|---|---|---|---|
| Yield (%) | 19.6 | 20.2 | 28.3 | 42.4 | 1.5 |
| Mn | 15,632 | 25,420 | 31,277 | 59,903 | — |
| Mw | 28,260 | 58,375 | 103,897 | 203,437 | — |
| r | 1.81 | 2.3 | 3.32 | 3.4 | — |

TABLE XXII

| Temperature (° C.) | 22 | 30 | 35 | 40 | 50 |
|---|---|---|---|---|---|
| Yield (%) | 42.5 | 32.5 | 28.3 | 25.2 | 5.5 |

Effect of Temperature on Enzyme Activity

To determine the effect of temperature on enzyme activity, the following experiment was performed over a range of temperatures. 700 μL water and 300 μL THF were mixed and degassed 15 minutes. 5.52 mmol styrene was added and the reaction was degassed for another 15 minutes. Next, 3.56× $10^{-4}$ mmol HRP was dissolved in 200 μL water and added into the reaction mixture. 0.0979 mmol 2,4-pentanedione and 0.196 mmol $H_2O_2$ were added together immediately after addition of the HRP. The reaction was allowed to proceed for 48 hours with shaking. A large excess of methanol to cause precipitation of the product, which was then filtered, washed with water, and dried.

TABLE XXIII

| Temperature (° C.) | 22 | 30 | 35 | 40 | 50 |
|---|---|---|---|---|---|
| HRP Active Time (hr) | 3.0 | 1.5 | 1.0 | 0.5 | 0.1 |

Exemplary Conditions for Polystyrene Synthesis a. Multiple $H_2O_2$ Additions at Room Temperature

| Parameters | Solvent | $H_2O$/Solvent (v/v) | [2,4-pentanedione] (mol/l) | Enzyme | [HRP] (units/ml) |
|---|---|---|---|---|---|
| Conditions | THF | 3:1 | 0.082 | HRP | 2667 |

| Parameters | $[H_2O_2]$ (mol/l) | $H_2O_2$ additions | Temperature (° C.) | Yield (%) | Mw | r |
|---|---|---|---|---|---|---|
| Conditions | 0.164 | 10 | 22 | 43.3 | 170,299 | 2.61 | b. Single $H_2O_2$ Addition At 40° C.

| Parameters | Solvent | $H_2O$/Solvent (v/v) | [2,4-pentanedione] (mol/l) | Enzyme | [HRP] (units/ml) |
|---|---|---|---|---|---|
| Conditions | THF | 3:1 | 0.082 | HRP | 2667 |

| Parameters | $[H_2O_2]$ (mol/l) | $H_2O_2$ additions | Temperature (° C.) | Yield (%) | Mw | r |
|---|---|---|---|---|---|---|
| Conditions | 0.164 | 1 | 40 | 42.4 | 203,437 | 3.4 |

Solubility of Polystyrene Products

Solubility data for a representative sample of polystyrene products set forth above are presented in Table XXIV.

TABLE XXIV

| Sample | Gel Fraction (Wg)(%) | Sol Fraction (Ws)(%) |
|---|---|---|
| $[H_2O_2]$/[RH] = 1:2 | 17.7 | 82.3 |
| $[H_2O_2]$/[RH] = 1:1 | 18.2 | 81.8 |
| $[H_2O_2]$/[RH] = 2:1 | 17.4 | 82.6 |
| Soybean Peroxidase | 15.2 | 84.8 |

DSC and FT-IR Study of Crystallization Behavior of Polystyrene

Conditions—~5 mg polystyrene samples were used each time. The scan rate was 10° C./min from 50° C. to 350° C. Indium was used for calibration. DSC results are presented in Table XXV. IR data is shown in Table XXVI.

TABLE XXV

| Samples | Tg(° C.) | Tm(° C.) |
|---|---|---|
| PS Standard (Mn = 47.5k), isotactic, amorphous | 104.54 | — |
| RH/$H_2O_2$ = 1:1, one addition $H_2O_2$ | 99.11 | — |
| RH/$H_2O_2$ = 1:1, 10 additions $H_2O_2$ | 99.38 | — |
| Isotactic Crystalline (Lit.) | 99 | 240 |
| Syndiotactic Crystalline (Lit.) | 100 | 270 |
| Atactic Polystyrene | 100 | — |

TABLE XXVI

| Samples | Characteristic Peaks | | |
|---|---|---|---|
| Isotactic Polystyrene | 1194 $cm^{-1}$ | 1312 $cm^{-1}$ | 1364 $cm^{-1}$ |
| Syndiotactic Polystyrene | 1220 $cm^{-1}$ | | |
| Polystyrene Sample | 1194 $cm^{-1}$ | 1312 $cm^{-1}$ | 1370 $cm^{-1}$ |

Styrene Crosslinking

Reaction conditions were varied from the standard conditions presented above to determine the impact of different variables on polymer cross-linking during the enzyme-mediated processes. Results are presented in Table XXVII. Unless otherwise noted, HRP was used as the enzyme.

TABLE XXVII

| Sample | Gel Fraction Ws (%) | Sol Fraction Wg (%) |
|---|---|---|
| $[H_2O]$/[RH] = 1:2 | 89.3 | 24.8 |
| $[H_2O]$/[RH] = 1:1 | 82.5 | 26.9 |
| $[H_2O]$/[RH] = 2:1 | 79.8 | 28 |
| Soybean Peroxidase | 85.5 | 14.5 |

Screening of Styrene Derivatives

A number of styrene derivatives were tested in the above polymerization reaction. Results are presented in Table XXVIII.

TABLE XXVIII

| COMPOUND | INITIATOR | YIELD | $CHCl_3$ SOLUBLE | $CHCl_3$ IN-SOLUBLE |
|---|---|---|---|---|
| STYRENE | 2,4-PD | 385 mg; 17% | 312 mg | 44 mg |
| PARA-METHYL STYRENE | 2,4-PD | 1.3 g; 45% | 998 mg | 80 mg |
| β-VINYL NAPHTHALENE | 2,4-PD | 3.5 g; 92% | 2.89 g | 78 mg |

All of the references and publications cited herein are hereby incorporated by reference.

Equivalents

Those skilled in the art will recognize, or be able to ascertain using no more than routine experimentation, numerous equivalents to the compounds and methods of use thereof described herein. Such equivalents are considered to be within the scope of this invention and are covered by the following claims.

We claim:

1. A method for polymerizing substituted ethylene monomers, comprising combining
    at least one substituted ethylene monomer,
    a peroxide source,
    an enzyme,
    a transfer agent, and
    an organic solvent wherein the reaction media is substantially free of water.
2. The method of claim 1, wherein the peroxide source is hydrogen peroxide.

3. The method of claim 1, wherein the enzyme is one of horseradish peroxidase, soybean peroxidase, and lignin peroxidase.

4. The method of claim 1, wherein the substituted ethylene monomer is one of methacrylate esters, acrylate esters, acrylamide, styrene, and acrylic acid and salts thereof.

5. The method of claim 1, wherein the organic solvent is tetrahydrofuran (THF), dimethyl formamide (DMF), acetone, or dioxane.

6. The method of claim 1, wherein the transfer agent comprises a β-dicarbonyl compound.

7. The method of claim 1, wherein the enzyme is a recombinant enzyme.

8. The method of claim 1, wherein the enzyme is a thermophilic enzyme.

9. The method of claim 1, wherein the enzyme is a mesophilic enzyme.

10. The method of claim 1, wherein the enzyme is active below 0° C.

11. A method for polymerizing substituted ethylene monomers, comprising combining under an inert atmosphere at least one substituted ethylene monomer, a peroxide source, an enzyme, and a transfer agent such that the polymerization is performed in the absence of oxygen.

12. The method of claim 11, wherein the peroxide source is hydrogen peroxide.

13. The method of claim 11, wherein the substituted ethylene monomer is one of methacrylate esters, acrylate esters, acrylamide, styrene, and acrylic acid and salts thereof.

14. The method of claim 11, wherein the transfer agent comprises a β-dicarbonyl compound.

15. The method of claim 11, wherein the method is performed using an emulsion.

16. The method of claim 11, wherein the method is performed using an inverse emulsion.

17. The method of claim 11, wherein the enzyme is selected from horseradish peroxidase, soybean peroxidase, and lignin peroxidase.

18. The method of claim 11, wherein the enzyme is a recombinant enzyme.

19. The method of claim 11, wherein the enzyme is a thermophilic enzyme.

20. The method of claim 11, wherein the enzyme is a mesophilic enzyme.

21. The method of claim 11, wherein the enzyme is active below 0° C.

22. The method of claim 12, wherein the enzyme is a thermophilic enzyme.

* * * * *